(12) United States Patent
Wu

(10) Patent No.: US 9,497,997 B2
(45) Date of Patent: Nov. 22, 2016

(54) INTEGRAL DISPOSABLE ELECTRONIC CIGARETTE

(71) Applicant: Shenzhen Smaco Technology Limited, Hong Kong (CN)

(72) Inventor: Yangyang Wu, Hong Kong (CN)

(73) Assignee: SHENZHEN SMACO TECHNOLOGY LIMITED, Shenzhen, Guangdong Province (CN)

( * ) Notice: Subject to any disclaimer, the term of this patent is extended or adjusted under 35 U.S.C. 154(b) by 336 days.

(21) Appl. No.: 14/186,449

(22) Filed: Feb. 21, 2014

(65) Prior Publication Data

US 2015/0208724 A1 Jul. 30, 2015

(30) Foreign Application Priority Data

Jan. 27, 2014 (CN) ...................... 2014 2 0052198 U

(51) Int. Cl.
*A24F 47/00* (2006.01)
*A61M 15/06* (2006.01)

(52) U.S. Cl.
CPC ............ *A24F 47/008* (2013.01); *A61M 15/06* (2013.01)

(58) Field of Classification Search
CPC ..................... A24F 47/00; A24F 47/002; A24F 47/004; A24F 47/008; A61M 15/06
See application file for complete search history.

(56) References Cited

U.S. PATENT DOCUMENTS

| 8,857,446 | B2* | 10/2014 | Wu | A24F 47/008 128/202.21 |
| 2011/0011396 | A1* | 1/2011 | Fang | A24F 47/008 128/202.21 |
| 2011/0303231 | A1* | 12/2011 | Li | A24F 47/008 131/329 |
| 2012/0145169 | A1* | 6/2012 | Wu | A24F 47/008 131/273 |
| 2014/0109921 | A1* | 4/2014 | Chen | A24F 47/008 131/273 |
| 2014/0182612 | A1* | 7/2014 | Chen | A24F 47/008 131/329 |
| 2015/0000684 | A1* | 1/2015 | Wu | A24F 47/008 131/329 |
| 2015/0034105 | A1* | 2/2015 | Liu | A24F 47/002 131/329 |
| 2015/0216232 | A1* | 8/2015 | Bless | A24F 47/008 131/328 |
| 2015/0216236 | A1* | 8/2015 | Bless | B23K 26/20 131/328 |

* cited by examiner

*Primary Examiner* — Anthony Calandra
(74) *Attorney, Agent, or Firm* — Cheng-Ju Chiang

(57) ABSTRACT

An integral disposable electronic cigarette may include an integral hollow cigarette where combustion can be arranged at a cigarette end position, so that the electronic cigarette is more similar to a non electronic cigarette; a lateral intake structure between the battery and the atomization plant may be adopted, which prevents an air flow from affecting normal use of the battery; moreover, a three seal ring structures can be adopted, which greatly improves the safety and reliability of the electronic cigarette.

9 Claims, 6 Drawing Sheets

INTEGRAL DISPOSABLE ELECTRONIC CIGARETTE

CROSS-REFERENCE TO RELATED APPLICATION

This application claims priority to the following patent application: (1) Chinese Patent Application CN201420052198.3 filed Jan. 27, 2014; the above cited application is hereby incorporated by reference herein as if fully set forth in its entirety.

TECHNICAL FIELD

The invention relates to an electronic cigarette, and in particular, to an integral lateral intake disposable electronic cigarette, which is closer to true cigarette, and is safer and more reliable.

BACKGROUND ART

It is well known that smoking does harm to health. Nicotine and tar in cigarette severely affect the health of people. Many countries start to legislate to ban smoking or ban to smoke in public places. However, there are still lots of smokers in each country at present, who are heavy smokers, highly rely on the cigarette and cannot give up smoking in a short time. Therefore, healthy and environmental-friendly electronic cigarettes are gradually popular to many smokers.

At present, all the electronic cigarettes frequently seen in the market consist of a battery component and an atomization plant, wherein the battery component is electrified to heat the tobacco tar to generate smoke so as to ease the addiction of the smokers. Partial or all the existing electronic cigarettes have the following disadvantages and defects:

1. All the existing electronic cigarettes are previous to light at the front end while being smoked, which are -inconvenient for a user to observe the working state of the electronic cigarette.
2. All the existing electronic cigarettes intake air from the most front end of the cigarettes, which are easy to age the battery since an air flow passes through the battery.
3. Most of the existing electronic cigarettes adopt a seal cover, which have high cost and is inconvenient to assemble.
4. The existing electronic cigarettes are not equipped with a protective board, which have low reliability.

SUMMARY OF THE INVENTION

In order to overcome the defects of the prior art, the invention aims at providing a safe and reliable integral disposable electronic cigarette which can shine through a lateral side of a cigarette end, and intake air from a lateral side of an atomization plant.

To achieve the above objective, the invention employs the technical scheme as follows:

an integral disposable electronic cigarette, includes
an integral hollow cigarette shell, wherein a lateral wall of the middle of the shell is provided with a radial intake through hole; a battery holding cavity is arranged on a portion from the intake through hole towards a cigarette end, and an atomization plant holding cavity is arranged on a portion from the intake through hole towards a cigarette holder;

a battery, which is internally arranged in the battery holding cavity of the shell, wherein a PCM (short for Pulse Code Modulation) board is arranged on the battery;

an illuminant, which is arranged at the cigarette end position of the shell, simulating cigarette combustion and illumination;

a hollow fixed seat, which is provided with a sealing end and a fixing end, wherein the sealing end is used for sealing and isolating the battery and the atomization plant, and the fixing end is used for fixing the atomization plant;

tobacco tar cotton, which is of a hollow structure, and used for storing the tobacco tar;

a U-shaped tar guide line, which is internally arranged in the tobacco tar cotton, wherein the bottom of the tar guide line is transversely arranged in a hollow pipe along a radial direction;

a heating filament, which is twisted on the bottom of the tar guide line in a non-contact manner, wherein the two ends of the heating filament are electrically connected with the battery;

a fiber pipe, wherein one end of the fiber pipe is arranged in the tobacco tar cotton, and the other end is sleeved at the fixing end of the hollow fixed seat; a position of the fiber pipe corresponding to the bottom of the tar guide line is provided with a radial through hole; and a portion of the tar guide line twisting the heating filament is arranged in the through hole; and a hollow rubber cover, which is provided with a rubber cover body in interference fit with the shell, and a bulge in interference fit with the fiber pipe.

Preferably, a lamp cap is arranged at the cigarette end of the shell. The lateral side of the lamp cap is pervious to light, and the end surface of the lamp cap shades light.

Preferably, a battery sticker layer is coated on the outer surface of the shell.

Preferably, a plastic cushion is arranged between the illuminant and the battery.

Preferably, the surface of the sealing end of the fixed seat is provided with annular grooves. Seal rings are correspondingly arranged in the annular grooves. A position of a lateral wall of the fixed seat corresponding to the intake through hole is provided with an annular groove. An intake through hole is arranged in the annular groove. An air flow passes through the intake through hole and the intake through hole, and enters the hollow pipe. The annular groove and the annular grooves are respectively arranged at the two sides of the intake through holes.

Preferably, the fixing end of the fixed seat is provided with an axial annual groove, and a portion of the fiber pipe sleeved at the fixed seat and exceeding the tobacco tar cotton is inserted in the annual groove.

Preferably, the cigarette holder end of the electronic cigarette is provided with a dustproof rubber cover.

Preferably, both the hollow rubber cover and the dust-proof rubber cover are manufactured by silica gel.

Since the foregoing structure is adopted, according to the integral disposable electronic cigarette of the invention, the illuminant simulating cigarette combustion is arranged at the cigarette end position, so that the electronic cigarette is closer to cigarette; a lateral intake structure between the battery and the atomization plant is adopted, which prevents the air flow from affecting normal use of the battery; moreover, three seal ring structures are adopted, which greatly improves the safety and reliability of the electronic cigarette.

DETAILED DESCRIPTION OF THE PREFERRED EMBODIMENTS

The invention is further introduced in details with references to the attached drawings and embodiments.

Figure 1:
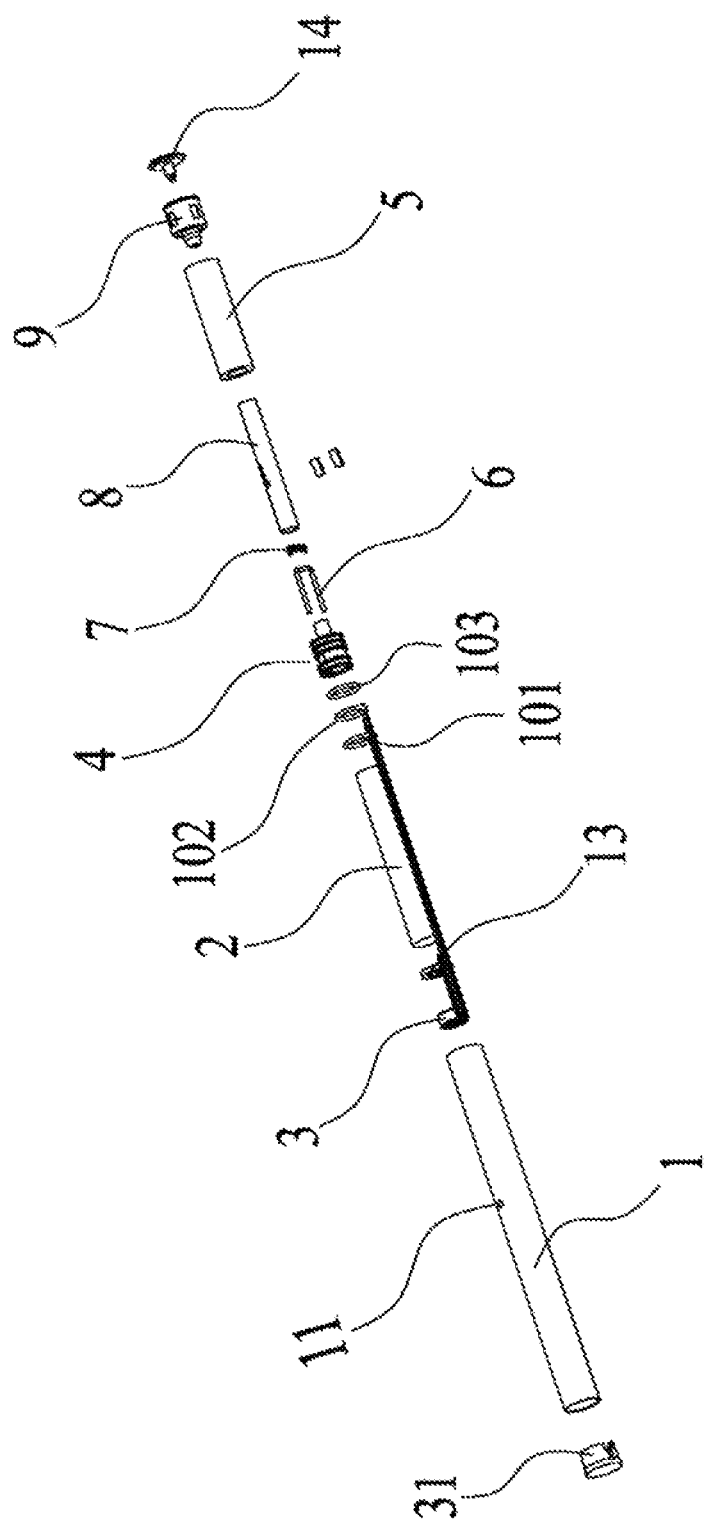
FIG. 1 is a structural explosion view of the invention.
Figure 2:
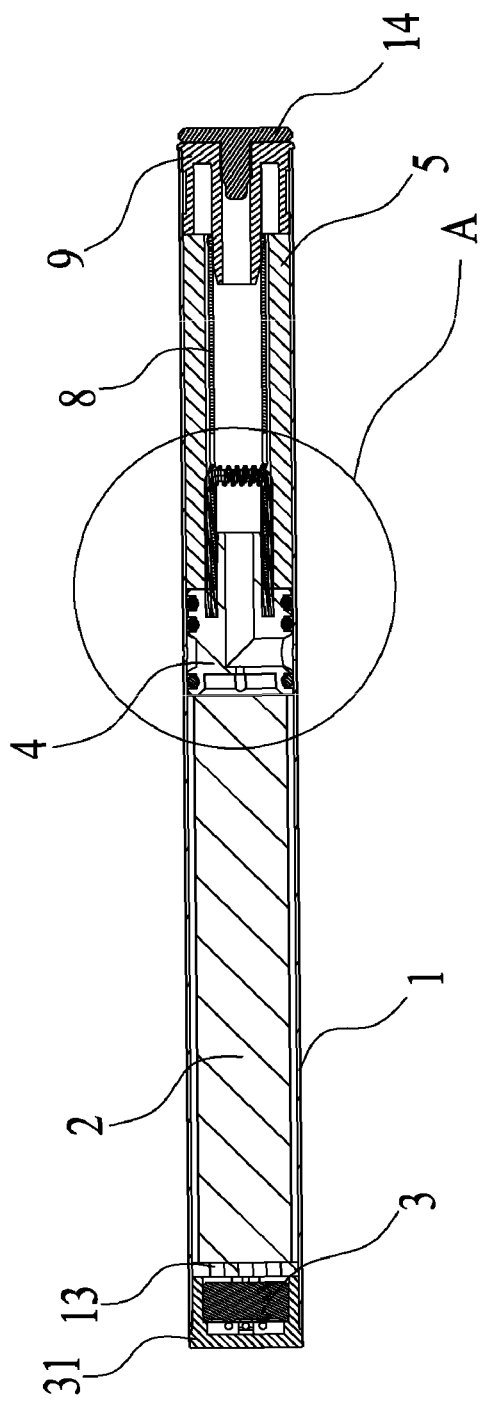
FIG. 2 is an axial section view of the invention.
Figure 3:
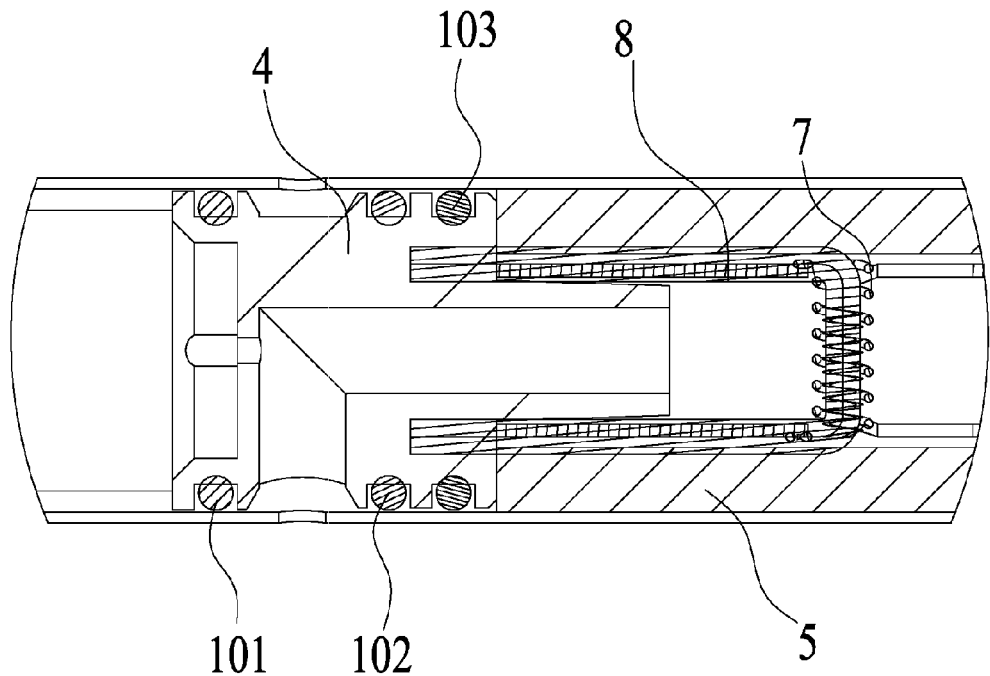
FIG. 3 is an enlarged schematic view of A in FIG. 2.
Figure 4:
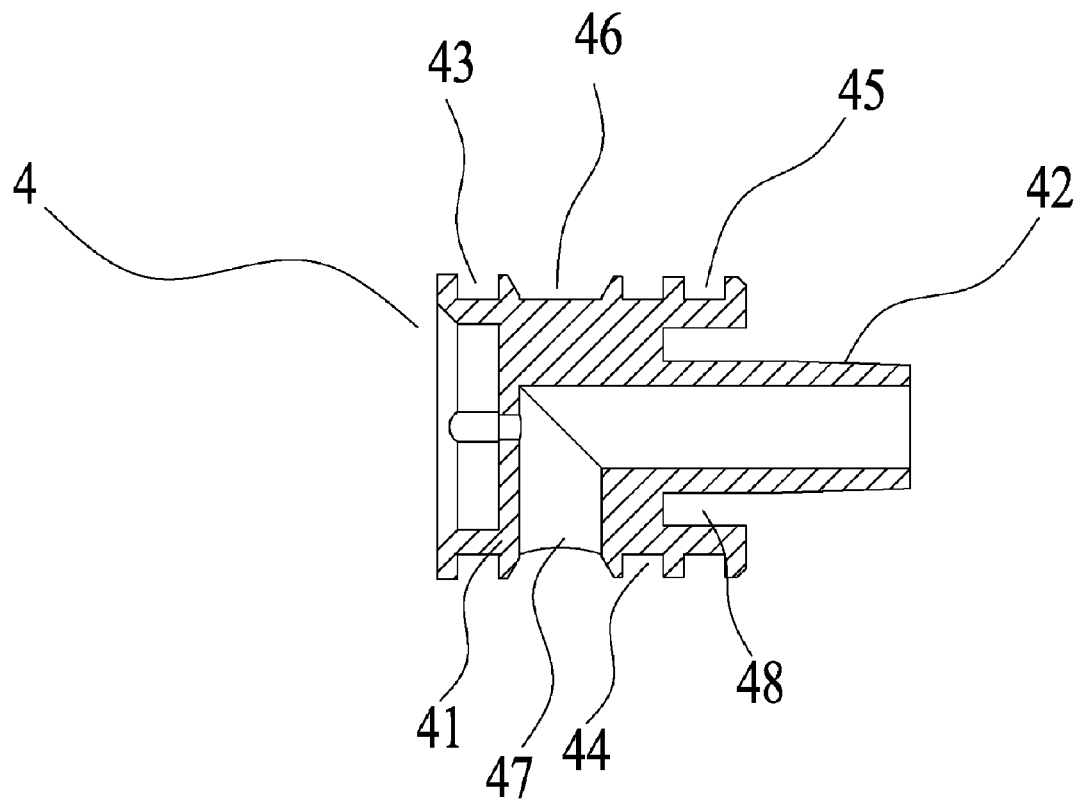
FIG. 4 is an axial section view of a fixed seat of the invention.
Figure 5:
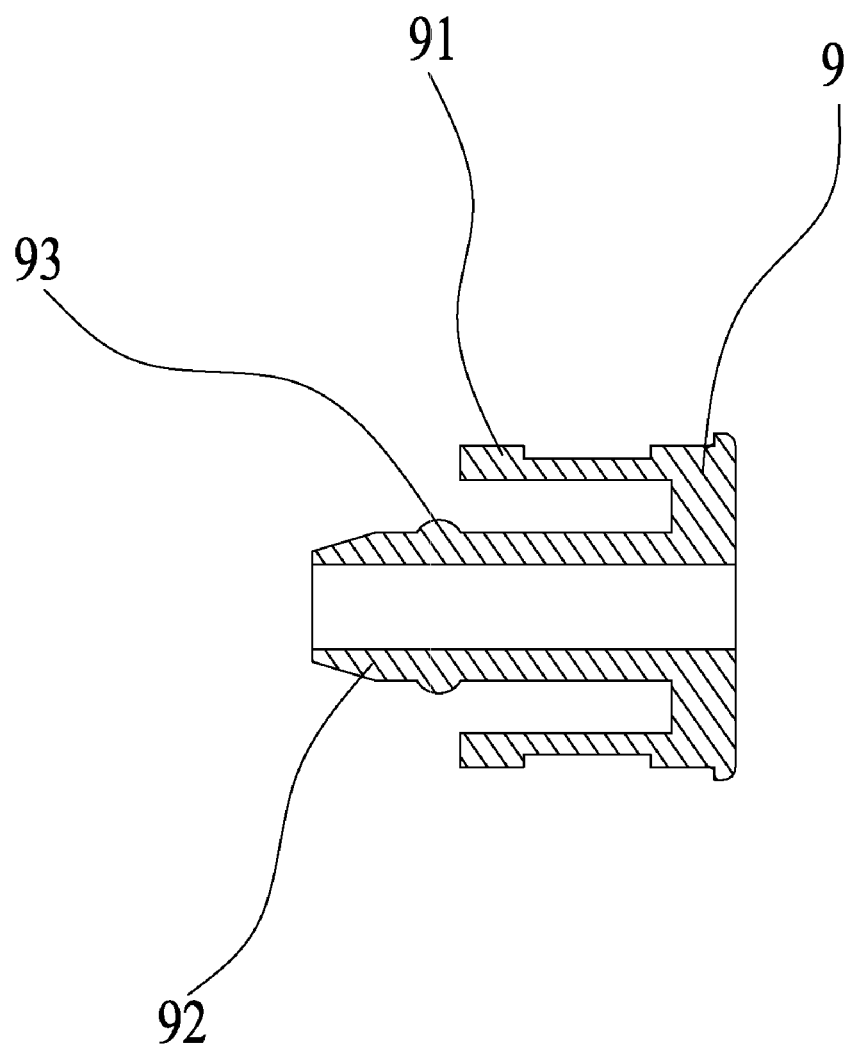
FIG. 5 is an axial section view of a hollow rubber cover of the invention.
Figure 6:
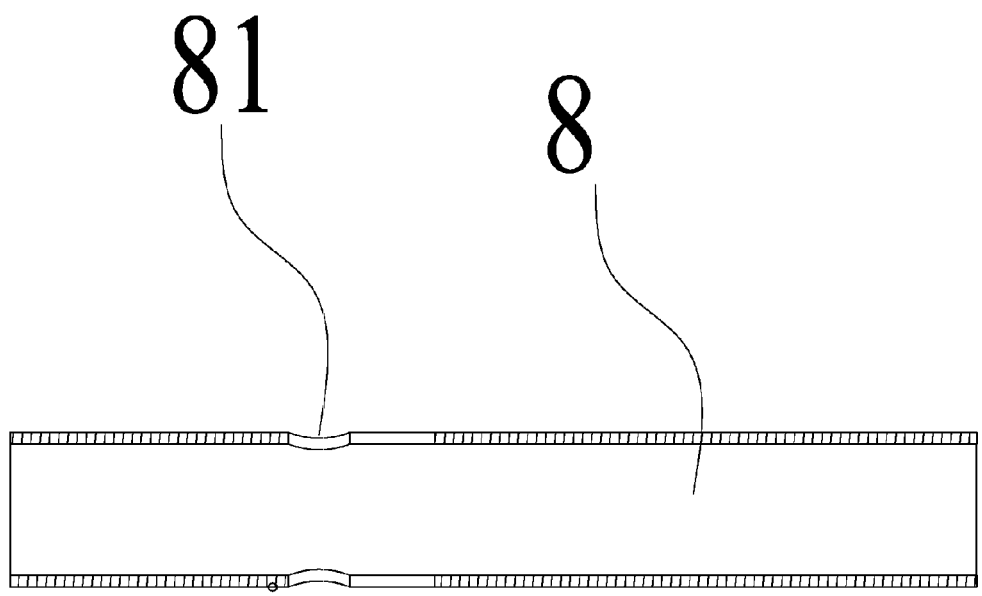
FIG. 6 is an axial section view of a fiber pipe of the invention.

FIGS. 1-6 show an integral disposable electronic cigarette, which includes an integral hollow cigarette shell 1. A battery sticker layer is coated on the outer surface of the shell 1. A lateral wall of the middle of the shell is provided with a radial intake through hole 11. A battery holding cavity is arranged on a portion from the intake through hole 11 towards a cigarette end and an atomization plant holding cavity is arranged on a portion from the intake through hole towards a cigarette holder. The shell 1 is provided with an illuminant 3, a plastic cushion 13, a battery 2, a hollow fixed seat 4 and an atomization plant in sequence from the cigarette end to the cigarette holder. The atomization plant includes tobacco tar cotton 5, a U-shaped tar guide line 6, a heating filament 7, a fiber pipe 8 and a hollow rubber cover 9. The battery 2 is internally arranged in the battery holding cavity of the shell 1. A PCM (short for Pulse Code Modulation) board is arranged on the battery 2. The illuminant 3 is arranged at the cigarette end position of the shell 1, simulating cigarette combustion and illumination.

The hollow fixed seat 4 is provided with a sealing end 41 and a fixing end 42. The sealing end 41 is used for sealing and isolating the battery and the atomization plant. The fixing end 42 is used for fixing the atomization plant. The surface of the sealing end 41 of the fixed seat 4 is provided with annular grooves 43, 44, 45. Seal rings 101, 102, 103 are correspondingly arranged in the annular grooves 43, 44, 45. A position of a lateral wall of the fixed seat 4 corresponding to the intake through hole 11 is provided with an annular groove 46. An intake through hole 47 is arranged in the annular groove 46. An air flow passes through the intake through hole 11 and the intake through hole 47, and enters the hollow pipe. The annular groove 43 and the annular grooves 44, 45 are respectively arranged at the two sides of the intake through holes 11, 47. In addition, the fixing end 42 of the fixed seat 4 is provided with an axial annual groove 48. A portion of the fiber pipe 8 sleeved at the fixed seat 4 and exceeding the tobacco tar cotton 5 is inserted in the annual groove 48.

The tobacco tar cotton 5 is also of a hollow structure, used for storing the tobacco tar. The U-shaped tar guide line 6 is internally arranged in the tobacco tar cotton 5, wherein the bottom of the tar guide line is transversely arranged in a hollow pipe along a radial direction and twisted by the heating filament 7 in a non-contact manner. The two ends of the heating filament 7 are electrically connected with the battery 2. One end of the fiber pipe 8 is arranged in the tobacco tar cotton 5, and the other end is sleeved at the fixing end 42 of the hollow fixed seat 4. A position of the fiber pipe 8 corresponding to the bottom of the tar guide line 6 is provided with a radial through hole 81. A portion of the tar guide line 6 twisting the heating filament 7 is arranged in the through hole 81. The hollow rubber cover 9 is provided with a rubber cover body 91 in interference fit with the shell 1, and a bulge 92 in interference fit (an annular seal ring 93 is arranged) with the fiber pipe 8. The outside of the hollow rubber cover 9 is further provided with a dustproof rubber cover 14. Both the hollow rubber cover 9 and the dustproof rubber cover 14 are manufactured by silica gel. A lamp cap 31 is arranged at the cigarette end of the shell 1. The lateral side of the lamp cap 31 is pervious to light, and the end surface of the lamp cap shades light.

The invention claimed is:

1. An integral disposable electronic cigarette, comprising:
   an integral hollow cigarette shell, wherein a lateral wall of the middle of the shell is provided with a radial intake through hole; a battery holding cavity is arranged on a portion from the intake through hole towards a first end of the electronic cigarette, and an atomization plant holding cavity is arranged on a portion from the intake through hole towards a second end of the electronic cigarette opposite to the first end;
   a battery, which is internally arranged in the battery holding cavity of the shell;
   an illuminant, which is arranged at the first end, configured for simulating cigarette combustion and illumination;
   a hollow fixed seat, which is provided with a sealing end and a fixing end, wherein the sealing end is configured for sealing and isolating the battery and the atomization plant, and the fixing end is configured for fixing the atomization plant;
   a tobacco tar cotton, which is of a hollow structure, and used for storing tobacco tar;
   a U-shaped tar guide line, which is internally arranged in the tobacco tar cotton, wherein the bottom of the U-shaped tar guide line is transversely arranged in a hollow pipe along a radial direction;
   a heating filament, which is twisted on the bottom of the U-shaped tar guide line in a non-contact manner, wherein the two ends of the heating filament are electrically connected with the battery;
   a fiber pipe, wherein one end of the fiber pipe is arranged in the tobacco tar cotton, and the other end is sleeved at the fixing end of the hollow fixed seat; a position of the fiber pipe corresponding to the bottom of the U-shaped tar guide line is provided with a radial through hole; and a portion of the U-shaped tar guide line twisting the heating filament is arranged in the through hole; and
   a hollow rubber cover, which is provided with a rubber cover body in interference fit with the shell, and a bulge in interference fit with the fiber pipe.

2. The integral disposable electronic cigarette according to claim 1, wherein a lamp cap is arranged at the first end; the lateral side of the lamp cap is pervious to light, and the end surface of the lamp cap blocks light.

3. The integral disposable electronic cigarette according to claim 1, wherein a sticker layer is coated on the outer surface of the shell.

4. The integral disposable electronic cigarette according to claim 1, wherein a plastic cushion is arranged between the illuminant and the battery.

5. The integral disposable electronic cigarette according to claim 1, wherein the fixing end of the fixed seat is provided with an axial annual groove, and a portion of the fiber pipe sleeved at the fixed seat and extending outside the tobacco tar cotton is inserted in the annual groove.

6. The integral disposable electronic cigarette according to claim 1, wherein the second end of the electronic cigarette is provided with a dustproof rubber cover.

7. The integral disposable electronic cigarette according to claim 1, wherein the hollow rubber cover is made of silica gel.

8. The integral disposable electronic cigarette according to claim 6, wherein the dustproof rubber cover is made of silica gel.

9. The integral disposable electronic cigarette according to claim 1, wherein a surface of the sealing end of the fixed seat is provided with first annular grooves; seal rings are correspondingly arranged in the first annular grooves; a position of a lateral wall of the fixed seat corresponding to the intake through hole of the shell is provided with a second annular groove; an intake through hole of the fixed seat is arranged in the second annular groove and is configured for an air flow to pass through the intake through hole of the shell and the intake through hole of the fixed seat, and to enter the hollow pipe; one of the first annular groove and others of the first annular grooves are respectively arranged at two sides of the intake through holes of the shell and the fixed seat.

* * * * *